US012773508B2

(12) United States Patent
Wilkerson et al.

(10) Patent No.: US 12,773,508 B2
(45) Date of Patent: Oct. 27, 2026

(54) SYSTEMS AND METHODS FOR PREDICTING MASK LEAKS

(71) Applicant: ResMed Sensor Technologies Limited, Dublin (IE)

(72) Inventors: Shawna Wilkerson, San Diego, CA (US); Ryan Mathew Hernandez, San Diego, CA (US); Gregory Robert Peake, San Diego, CA (US); Redmond Shouldice, Dublin (IE); Stephen McMahon, Dublin (IE)

(73) Assignee: ResMed Sensor Technologies Limited, Dublin (IE)

( * ) Notice: Subject to any disclaimer, the term of this patent is extended or adjusted under 35 U.S.C. 154(b) by 909 days.

(21) Appl. No.: 18/000,229

(22) PCT Filed: May 29, 2021

(86) PCT No.: PCT/US2021/035044
§ 371 (c)(1),
(2) Date: Nov. 29, 2022

(87) PCT Pub. No.: WO2021/243316
PCT Pub. Date: Dec. 2, 2021

(65) Prior Publication Data

US 2023/0191053 A1 Jun. 22, 2023

Related U.S. Application Data

(60) Provisional application No. 63/032,325, filed on May 29, 2020.

(51) Int. Cl.
*A61M 16/00* (2006.01)
*A61B 5/00* (2006.01)
(Continued)

(52) U.S. Cl.
CPC ...... *A61M 16/022* (2017.08); *A61M 16/0003* (2014.02); *A61M 16/0666* (2013.01);
(Continued)

(58) Field of Classification Search
CPC ........... A61M 2205/15; A61M 16/022; A61M 16/0003; A61M 16/0666; A61M 16/161;
(Continued)

(56) References Cited

U.S. PATENT DOCUMENTS

2004/0187871 A1 9/2004 Kimmel et al.
2006/0174883 A1 8/2006 Aylsworth et al.
(Continued)

FOREIGN PATENT DOCUMENTS

CN 104884113 A 9/2015
JP H08257016 A 10/1996
(Continued)

OTHER PUBLICATIONS

International Search Report in International Patent Application No. PCT/US21/35044 mailed Sep. 24, 2021 (4 pp.).
(Continued)

*Primary Examiner* — Valerie L Woodward
*Assistant Examiner* — Mautin I Ashimiu
(74) *Attorney, Agent, or Firm* — NIXON PEABODY LLP

(57) ABSTRACT

A method of predicting an unintentional leak in a respiratory system during a sleep session includes causing, during the sleep session, pressurized air to be delivered from a respiratory device to a user via a conduit coupled to a user interface. The method also includes receiving historical first data associated with pressurized air delivered from the respiratory device during one or more prior sleep sessions; receiving current first data associated with the pressurized air being delivered from the respiratory device during the sleep session; receiving historical second data associated
(Continued)

with the user during one or more prior sleep sessions; and receiving, via one or more second sensors, current second data associated with the user during the current sleep session. The method determines, a likelihood that an unintentional leak in the respiratory system will occur within a predetermined amount of time.

16 Claims, 4 Drawing Sheets

(51) Int. Cl.
*A61B 5/08* (2006.01)
*A61M 16/06* (2006.01)
*A61M 16/16* (2006.01)

(52) U.S. Cl.
CPC ....... *A61M 16/161* (2014.02); *A61M 2205/15* (2013.01); *A61M 2205/3331* (2013.01); *A61M 2205/44* (2013.01)

(58) Field of Classification Search
CPC ...... A61M 2205/3331; A61M 2230/62; A61M 2016/0027; A61M 2016/0033; A61M 16/16; A61M 16/0051; A61M 16/026; A61M 2205/18; A61M 16/06–0694; A61B 5/4806–4818; A61B 5/0826; A61B 5/0816; A61B 5/4815; A61B 5/6814; A61B 5/4836
See application file for complete search history.

(56) References Cited

U.S. PATENT DOCUMENTS

| | | | | |
|---|---|---|---|---|
| 2011/0259330 | A1 | 10/2011 | Jafari et al. | |
| 2014/0002246 | A1 | 1/2014 | Steinhauer et al. | |
| 2015/0367092 | A1* | 12/2015 | Goff | A61B 5/4818 128/204.23 |
| 2017/0239432 | A1* | 8/2017 | Delangre | A61M 16/06 |
| 2017/0312123 | A1* | 11/2017 | Coleman | A61M 16/0463 |
| 2017/0361045 | A1* | 12/2017 | Fu | A61M 16/0066 |
| 2018/0344961 | A1* | 12/2018 | Thompson | A61M 16/0666 |

FOREIGN PATENT DOCUMENTS

| | | | |
|---|---|---|---|
| JP | 2009506833 | A | 2/2009 |
| WO | 2015/196255 | A1 | 12/2015 |
| WO | 2018/050913 | A1 | 3/2018 |

OTHER PUBLICATIONS

Written Opinion in International Patent Application No. PCT/US21/35044 mailed Sep. 24, 2021 (8 pp.).

* cited by examiner

SYSTEMS AND METHODS FOR PREDICTING MASK LEAKS

CROSS-REFERENCE TO RELATED APPLICATIONS

This application is a U.S. National Stage of International Application No. PCT/US2021/035044, filed on May 29, 2021, which claims the benefit of and priority to U.S. Provisional Patent Application No. 63/032,325, filed May 29, 2020, the contents of which are hereby incorporated by reference herein in their entireties.

TECHNICAL FIELD

The present disclosure relates generally to respiratory systems and more particularly to systems and methods for predicting unintentional mask leaks in respiratory systems.

BACKGROUND

Many individuals suffer from sleep-related and/or respiratory disorders such as, for example, Periodic Limb Movement Disorder (PLMD), Restless Leg Syndrome (RLS), Sleep-Disordered Breathing (SDB), Obstructive Sleep Apnea (OSA), apneas, Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders. These disorders are often treated using a respiratory therapy system. A person with respiratory disorder can have trouble sleeping, but systems designed to mitigate physical symptoms of the respiratory disorder do not address issues outside of the symptoms of the disorder itself that can keep the person from sleeping well. Thus, a need exists for alternative systems and methods for addressing sleep disturbances or unintentional features of current respiratory therapy systems that can degrade the quality of the intended sleep therapy. The present disclosure is directed to solving these problems and addressing other needs.

SUMMARY

According to some implementations of the present disclosure, a method of predicting an unintentional leak in a respiratory system during a current sleep session includes causing, during the current sleep session, pressurized air to be delivered from a respiratory device to a user via a conduit coupled to a user interface. The user interface is worn about a portion of a face of the user to aid in the user receiving at least a portion of the pressurized air. Historical first data associated with pressurized air delivered from the respiratory device during one or more prior sleep sessions is received. Current first data associated with the pressurized air being delivered from the respiratory device during the current sleep session is received, via one or more first sensors. Historical second data associated with one or more orientations of the user during one or more prior sleep sessions is received. Current second data associated with one or more orientations of the user during the current sleep session is received, via one or more second sensors. Based at least in part on the (i) historical first data, (ii) the current first data, (iii) the historical second data, and (iv) the current second data, a likelihood that an unintentional leak in the respiratory system will occur within a predetermined amount of time is determined.

According to some implementations of the present disclosure, a method of predicting an unintentional leak in a respiratory system during a current sleep session includes determining, for a user of the respiratory system, an unintentional leak prediction value. The determined unintentional leak prediction value is indicative of a likelihood that the user will experience an unintentional leak within a pre-determined amount of time in the current sleep session. The unintentional leak prediction value is determined using an unintentional leak prediction algorithm that is configured to receive, as an input, positional data, and output the unintentional leak prediction value for the individual.

The above summary is not intended to represent each implementation or every aspect of the present disclosure. Additional features and benefits of the present disclosure are apparent from the detailed description and figures set forth below.

Figure 1:
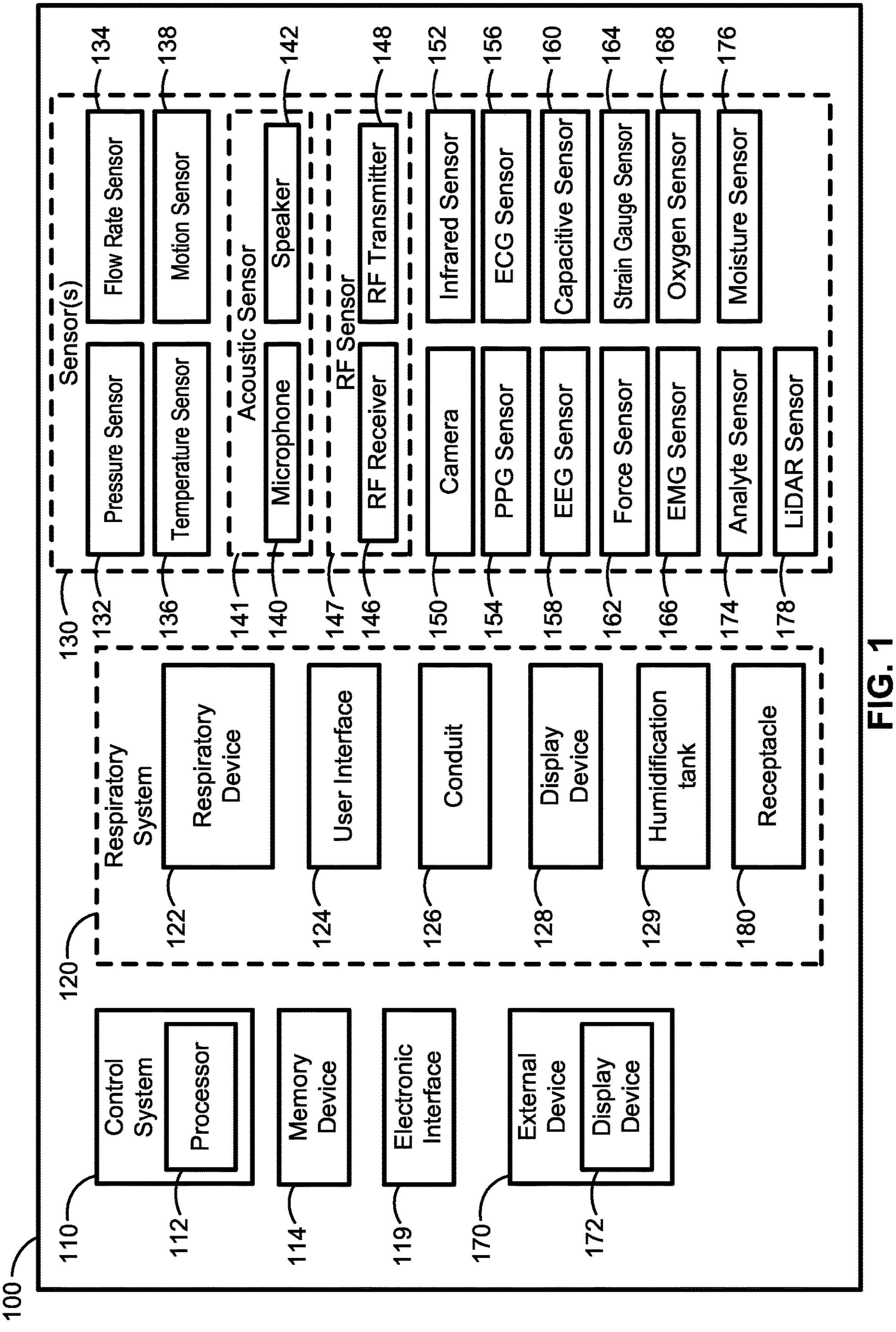
FIG. 1 is a functional block diagram of a system, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Many individuals suffer from sleep-related and/or respiratory disorders. Examples of sleep-related and/or respiratory disorders include Periodic Limb Movement Disorder (PLMD), Restless Leg Syndrome (RLS), Sleep-Disordered Breathing (SDB), Obstructive Sleep Apnea (OSA), apneas, Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders.

In order to mitigate some of these sleep-related and/or respiratory disorders, a user can be prescribed usage of a respiratory device or system. For example, a continuous positive airway pressure (CPAP) machine can be used to increase air pressure in the throat of the respiratory device user (e.g., user) and to prevent the airway from closing and/or narrowing during sleep. While these respiratory devices or systems can improve the sleep quality of the user some issues outside of the symptoms of the disorder itself that can work counter to the sought after sleep quality improvement. For example, noises due to the system such as produced by unintentional leaks. As well as possibly reducing the sleep quality of the user, such noises can also disturb the quality of a sleep partner. In some implementations of the present disclosure, a method for predicting an unintentional leak in a respiratory system used by a subject during a current sleep session is described. Prediction of an unintentional leak allows a mitigating action to stop an unintentional leak can be implemented.

Referring to FIG. 1, a system 100, according to some implementations of the present disclosure, is illustrated. The system 100 includes a control system 110, a memory device 114, an electronic interface 119, one or more sensors 130, and one or more user devices 170. In some implementation, the system 100 further optionally includes a respiratory system 120.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 can be coupled to and/or positioned within, for example, a housing of the user device 170, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory device 122, within a housing of the user device 170, within a housing of one or more of the sensors 130, or any combination thereof. Like the control system 110, the memory device 114 can be centralized (within one such housing) or decentralized (within two or more of such housings, which are physically distinct).

In some implementations, the memory device 114 (FIG. 1) stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family history of insomnia, an employment status of the user, an educational status of the user, a socioeconomic status of the user, or any combination thereof. The medical information can include, for example, including indicative of one or more medical conditions associated with the user, medication usage by the user, or both. The medical information data can further include a multiple sleep latency test (MSLT) test result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a WiFi communication protocol, a Bluetooth communication protocol, over a cellular network, etc.). The electronic interface 119 can include an antenna, a receiver (e.g., an RF receiver), a transmitter (e.g., an RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the user device 170. In other implementations, the electronic interface 119 is coupled to or integrated (e.g., in a housing) with the control system 110 and/or the memory device 114.

As noted above, in some implementations, the system 100 optionally includes a respiratory system 120 (also referred to as a respiratory therapy system). The respiratory system 120 can include a respiratory pressure therapy device 122 (referred to herein as respiratory device 122), a user interface 124, a conduit 126 (also referred to as a tube or an air circuit), a display device 128, a humidification tank 129, a receptacle 180 or any combination thereof. In some implementations, the control system 110, the memory device 114, the display device 128, one or more of the sensors 130, and the humidification tank 129 are part of the respiratory device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory system 120 is generally used to treat individuals suffering from one or more sleep-related respiratory disorders (e.g., obstructive sleep apnea, central sleep apnea, or mixed sleep apnea).

The respiratory device 122 is generally used to generate pressurized air that is delivered to a user (e.g., using one or more motors that drive one or more compressors). In some implementations, the respiratory device 122 generates continuous constant air pressure that is delivered to the user. In other implementations, the respiratory device 122 generates two or more predetermined pressures (e.g., a first predetermined air pressure and a second predetermined air pressure). In still other implementations, the respiratory device 122 is configured to generate a variety of different air pressures within a predetermined range. For example, the respiratory device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory device 122 can also deliver pressurized air at a predetermined flow rate between, for example, about-20 L/min and about 150 L/min, while maintaining a positive pressure (relative to the ambient pressure).

The user interface 124 engages a portion of the user's face and delivers pressurized air from the respiratory device 122 to the user's airway to aid in preventing the airway from narrowing and/or collapsing during sleep. This may also increase the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm $H_2O$.

Figure 2:
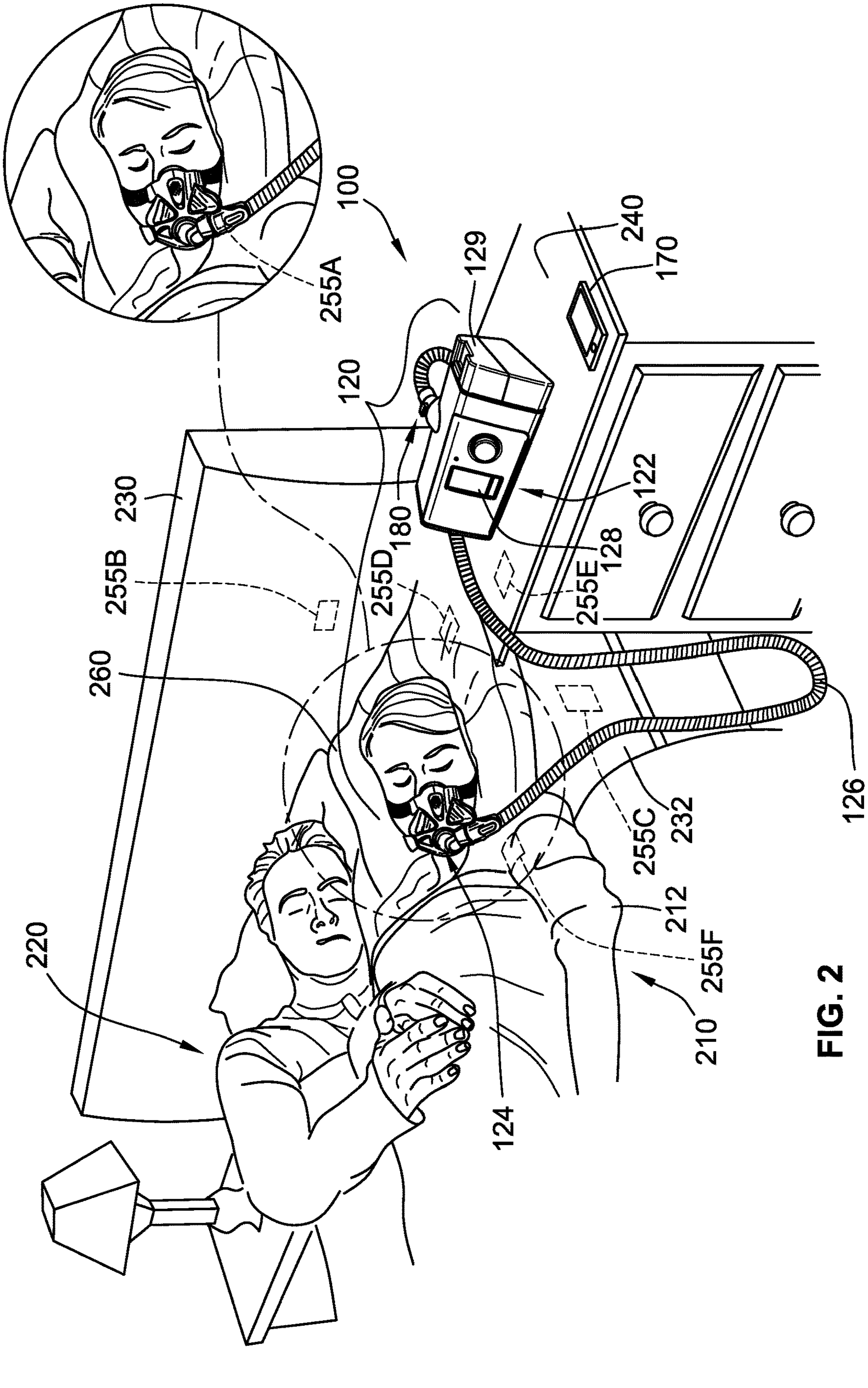
FIG. 2 is a perspective view of at least a portion of the system of FIG. 1, a user, and a bed partner, according to some implementations of the present disclosure.

As shown in FIG. 2, in some implementations, the user interface 124 is a facial mask (e.g., a full face mask) that covers the nose and mouth of the user. The user interface 124 can include a plurality of straps (e.g., including hook and loop fasteners) for positioning and/or stabilizing the interface on a portion of the user (e.g., the face) and a conformal cushion (e.g., silicone, plastic, foam, etc.) intended to provide an air-tight seal between the user interface 124 and the user. The user interface 124 can also include one or more vents for permitting the escape of carbon dioxide and other gases exhaled by the user 210.

The conduit 126 (also referred to as an air circuit or tube) allows the flow of air between two components of a respiratory system 120, such as the respiratory device 122 and the user interface 124. In some implementations, there can be separate limbs of the conduit for inhalation and exhalation. In other implementations, a single limb conduit is used for both inhalation and exhalation.

One or more of the respiratory device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be used, for example, to measure the air pressure and/or flow rate of pressurized air supplied by the respiratory device 122.

The display device 128 is generally used to display image(s) including still images, video images, or both and/or information regarding the respiratory device 122. For example, the display device 128 can provide information regarding the status of the respiratory device 122 (e.g., whether the respiratory device 122 is on/off, the pressure of the air being delivered by the respiratory device 122, the temperature of the air being delivered by the respiratory device 122, etc.) and/or other information (e.g., a sleep score, the current date/time, personal information for the user 210, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory device 122.

The humidification tank 129 is coupled to or integrated in the respiratory device 122. The humidification tank 129 includes a reservoir of water that can be used to humidify the pressurized air delivered from the respiratory device 122. The respiratory device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user. The humidification tank 129 can be fluidly coupled to a water vapor inlet of the air pathway and deliver water vapor into the air pathway via the water vapor inlet, or can be formed in-line with the air pathway as part of the air pathway itself.

In some implementations, the system 100 can be used to deliver at least a portion of a substance from a receptacle 180 to the air pathway the user based at least in part on the physiological data, the sleep-related parameters, other data or information, or a combination thereof. Generally, modifying the delivery of the portion of the substance into the air pathway can include (i) initiating the delivery of the substance into the air pathway, (ii) ending the delivery of the portion of the substance into the air pathway, (iii) modifying an amount of the substance delivered into the air pathway, (iv) modifying a temporal characteristic of the delivery of the portion of the substance into the air pathway, (v) modifying a quantitative characteristic of the delivery of the portion of the substance into the air pathway, (vi) modifying any parameter associated with the delivery of the substance into the air pathway, or (vii) a combination of (i)-(vi).

Modifying the temporal characteristic of the delivery of the portion of the substance into the air pathway can include changing the rate at which the substance is delivered, starting and/or finishing at different times, continuing for different time periods, changing the time distribution or characteristics of the delivery, changing the amount distribution independently of the time distribution, etc. The independent time and amount variation ensures that, apart from varying the frequency of the release of the substance, one can vary the amount of substance released each time. In this manner, a number of different combination of release frequencies and release amounts (e.g., higher frequency but lower release amount, higher frequency and higher amount, lower frequency and higher amount, lower frequency and lower amount, etc.) can be achieved. Other modifications to the delivery of the portion of the substance into the air pathway can also be utilized.

The respiratory system 120 can be used, for example, as a positive airway pressure (PAP) system, a continuous positive airway pressure (CPAP) system, an automatic positive airway pressure system (APAP), a bi-level or variable positive airway pressure system (BPAP or VPAP), a ventilator, or a combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Still referring to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a Light Detection and Ranging (LiDAR) sensor 178, or a combination thereof. Generally, each of the one or more sensors 130 are configured to output sensor data that is received and stored in the memory device 114 or one or more other memory devices.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the infrared sensor 152, the photoplethysmogram (PPG) sensor 154, the electrocardiogram (ECG) sensor 156, the electroencephalography (EEG) sensor 158, the capacitive sensor 160, the force sensor 162, the strain gauge sensor 164, the electromyography (EMG) sensor 166, the oxygen sensor 168, the analyte sensor 174, the moisture sensor 176, and the Light Detection and Ranging (LiDAR) sensor 178 more generally, the one or more sensors 130 can include a combination and any number of each of the sensors described and/or shown herein.

As described herein, the system 100 generally can be used to generate physiological data associated with a user (e.g., a user of the respiratory system 120 shown in FIG. 2) during a sleep session. The physiological data can be analyzed to generate one or more sleep-related parameters, which can include any parameter, measurement, etc. related to the user during the sleep session. The one or more sleep-related parameters that can be determined for the user 210 during the sleep session include, for example, an Apnea-Hypopnea Index (AHI) score, a sleep score, a flow signal, a respiration signal, a respiration rate, an inspiration amplitude, an expiration amplitude, an inspiration-expiration ratio, a number of events per hour, a pattern of events, a stage, pressure settings of the respiratory device 122, a heart rate, a heart rate variability, movement of the user 210, temperature, EEG activity, EMG activity, arousal, snoring, choking, coughing, whistling, wheezing, or a combination thereof.

In some implementations, the physiological data generated by one or more of the sensors 130 can be used by the control system 110 to determine a sleep-wake signal associated with the user 210 during the sleep session and one or more sleep-related parameters. The sleep-wake signal can be indicative of one or more sleep states, including wakefulness, relaxed wakefulness, micro-awakenings, a rapid eye movement (REM) stage, a first non-REM stage (often referred to as "N1"), a second non-REM stage (often referred to as "N2"), a third non-REM stage (often referred to as "N3"), or a combination thereof.

The sleep-wake signal can also be timestamped to determine a time that the user enters the bed, a time that the user exits the bed, a time that the user attempts to fall asleep, etc. The sleep-wake signal can be measured by the one or more sensors 130 during the sleep session at a predetermined sampling rate, such as, for example, one sample per second, one sample per 30 seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory device 122, or a combination thereof during the sleep session. The event(s) can include snoring, apneas, central apneas, obstructive apneas, mixed apneas, hypopneas, a mask leak (e.g., from the user interface 124), a restless leg, a sleeping disorder, choking, an increased heart rate, labored breathing, an asthma attack, an epileptic episode, a seizure, or a combination thereof. The one or more sleep-related parameters that can be determined for the user during the sleep session based on the sleep-wake signal include, for example, a total time in bed, a total sleep time, a sleep onset latency, a wake-after-sleep-onset parameter, a sleep efficiency, a fragmentation index, or a combination thereof.

Generally, the sleep session includes any point in time after the user 210 has laid or sat down in the bed 230 (or another area or object on which they intend to sleep), and/or has turned on the respiratory device 122 and/or donned the user interface 124. The sleep session can thus include time periods (i) when the user 210 is using the CPAP system but before the user 210 attempts to fall asleep (for example when the user 210 lays in the bed 230 reading a book); (ii) when the user 210 begins trying to fall asleep but is still awake; (iii) when the user 210 is in a light sleep (also referred to as stage 1 and stage 2 of non-rapid eye movement (NREM) sleep); (iv) when the user 210 is in a deep sleep (also referred to as slow-wave sleep, SWS, or stage 3 of NREM sleep); (v) when the user 210 is in rapid eye movement (REM) sleep; (vi) when the user 210 is periodically awake between light sleep, deep sleep, or REM sleep; or (vii) when the user 210 wakes up and does not fall back asleep.

The sleep session is generally defined as ending once the user 210 removes the user interface 124, turns off the respiratory device 122, and/or gets out of bed 230. In some implementations, the sleep session can include additional periods of time, or can be limited to only some of the above-disclosed time periods. For example, the sleep session can be defined to encompass a period of time beginning when the respiratory device 122 begins supplying the pressurized air to the airway or the user 210, ending when the respiratory device 122 stops supplying the pressurized air to the airway of the user 210, and including some or all of the time points in between, when the user 210 is asleep or awake.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory system 120 and/or ambient pressure. In such implementations, the pressure sensor 132 can be coupled to or integrated in the respiratory device 122. The pressure sensor 132 can be, for example, a capacitive sensor, an electromagnetic sensor, a piezoelectric sensor, a strain-gauge sensor, an optical sensor, a potentiometric sensor, or a combination thereof.

The flow rate sensor 134 outputs flow rate data that can be stored in the memory device 114 and/or analyzed by the processor 112 of the control system 110. In some implementations, the flow rate sensor 134 is used to determine an air flow rate from the respiratory device 122, an air flow rate through the conduit 126, an air flow rate through the user interface 124, or a combination thereof. In such implementations, the flow rate sensor 134 can be coupled to or integrated in the respiratory device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or a combination thereof.

The temperature sensor 136 outputs temperature data that can be stored in the memory device 114 and/or analyzed by the processor 112 of the control system 110. In some implementations, the temperature sensor 136 generates temperatures data indicative of a core body temperature of the user 210 (FIG. 2), a skin temperature of the user 210, a temperature of the air flowing from the respiratory device 122 and/or through the conduit 126, a temperature in the user interface 124, an ambient temperature, or a combination thereof. The temperature sensor 136 can be, for example, a thermocouple sensor, a thermistor sensor, a silicon band gap temperature sensor or semiconductor-based sensor, a resistance temperature detector, or a combination thereof.

The motion sensor 138 outputs motion data that can be stored in the memory device 114 and/or analyzed by the processor 112 of the control system 110. The motion sensor 138 can be used to detect movement of the user 210 during the sleep session, and/or detect movement of any of the components of the respiratory system 120, such as the respiratory device 122, the user interface 124, or the conduit 126. The motion sensor 138 can include one or more inertial sensors, such as accelerometers, gyroscopes, and magnetometers. In some implementations, the motion sensor 138 alternatively or additionally generates one or more signals representing bodily movement of the user, from which may be obtained a signal representing a sleep state of the user; for example, via a respiratory movement of the user. In some implementations, the motion data from the motion sensor 138 can be used in conjunction with additional data from another sensor 130 to determine the sleep state of the user.

The microphone 140 outputs sound data that can be stored in the memory device 114 and/or analyzed by the processor 112 of the control system 110. The microphone 140 can be used to record sound(s) during a sleep session (e.g., sounds from the user 210) to determine (e.g., using the control system 110) one or more sleep-related parameters, as described in further detail herein. The microphone 140 can be coupled to or integrated in the respiratory device 122, the user interface 124, the conduit 126, or the user device 170. In some implementations, the system 100 includes a plurality of microphones (e.g., two or more microphones and/or an array of microphones with beamforming) such that sound data generated by each of the plurality of microphones can be used to discriminate the sound data generated by another of the plurality of microphones.

The speaker 142 outputs sound waves that are audible to a user of the system 100 (e.g., the user 210 of FIG. 2). The speaker 142 can be used, for example, as an alarm clock or to play an alert or message to the user 210 (e.g., in response to an event such as an unintentional mask leak). The speaker 142 can be coupled to or integrated in the respiratory device 122, the user interface 124, the conduit 126, or the external device 170.

The microphone 140 and the speaker 142 can be used as separate devices. In some implementations, the microphone 140 and the speaker 142 can be combined into an acoustic sensor 141, as described in, for example, WO 2018/050913, which is hereby incorporated by reference herein in its entirety. In such implementations, the speaker 142 generates or emits sound waves at a predetermined interval and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user 210 or the bed partner 220 (FIG. 2). Based at least in part on the data from the microphone 140 and/or the speaker 142, the control system 110 can determine a location or orientation of the user 210 (FIG. 2) and/or one or more of the sleep-related parameters described in herein.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user 210 (FIG. 2) and/or one or more of the sleep-related parameters described herein. An RF receiver (either the RF receiver 146 and the RF transmitter 148 or another RF pair) can also be used for wireless communication between the control system 110, the respiratory device 122, the one or more sensors 130, the user device 170, or a combination thereof. While the RF receiver 146 and RF transmitter 148 are shown as being separate and distinct elements in FIG. 1, in some implementations, the RF receiver 146 and RF transmitter 148 are combined as a part of an RF sensor 147. In some such implementations, the RF sensor 147 includes a control circuit. The specific format of the RF communication could be Wi-Fi, Bluetooth, etc.

In some implementations, the RF sensor 147 is a part of a mesh system. One example of a mesh system is a Wi-Fi mesh system, which can include mesh nodes, mesh router(s), and mesh gateway(s), each of which can be mobile/movable or fixed. In such implementations, the Wi-Fi mesh system includes a Wi-Fi router and/or a Wi-Fi controller and one or more satellites (e.g., access points), each of which include an RF sensor that the is the same as, or similar to, the RF sensor 147. The Wi-Fi router and satellites continuously communicate with one another using Wi-Fi signals. The Wi-Fi mesh system can be used to generate motion data based on changes in the Wi-Fi signals (e.g., differences in received signal strength) between the router and the satellite(s) due to an object or person moving partially obstructing the signals. The motion data can be indicative of motion, breathing, heart rate, behavior, etc., or a combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein, such as, for example, one or more events (e.g., position change of subject 210), a respiration signal, a respiration rate, an inspiration amplitude, an expiration amplitude, an inspiration-expiration ratio, a number of events per hour, a pattern of events, a sleep state, a sleep stage, or a combination thereof. Further, the image data from the camera 150 can be used to, for example, identify a position and orientation of the user, to determine chest movement of the user 210, to determine air flow of the mouth and/or nose of the user 210, to determine a time when the user 210 enters the bed 230, and to determine a time when the user 210 exits the bed 230.

The infrared (IR) sensor 152 outputs infrared image data reproducible as one or more infrared images (e.g., still images, video images, or both) that can be stored in the memory device 114. The infrared data from the IR sensor 152 can be used to determine one or more sleep-related parameters during a sleep session, including a temperature of the user 210 and/or movement of the user 210. The IR sensor 152 can also be used in conjunction with the camera 150 when measuring the presence, location, and/or movement of the user 210. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user 210 (FIG. 2) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or a combination thereof. The PPG sensor 154 can be worn by the user 210, embedded in clothing and/or fabric that is worn by the user 210, embedded in and/or coupled to the user interface 124 and/or its associated headgear (e.g., straps, etc.), etc.

The ECG sensor 156 outputs physiological data associated with electrical activity of the heart of the user 210 (FIG. 2A). In some implementations, the ECG sensor 156 includes one or more electrodes that are positioned on or around a portion of the user 210 during the sleep session. The physiological data from the ECG sensor 156 can be used, for example, to determine one or more of the sleep-related parameters described herein.

The EEG sensor 158 outputs physiological data associated with electrical activity of the brain of the user 210. In some implementations, the EEG sensor 158 includes one or more electrodes that are positioned on or around the scalp of the user 210 during the sleep session. The physiological data from the EEG sensor 158 can be used, for example, to determine a sleep state of the user 210 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or a combination thereof.

The analyte sensor 174 can be used to detect the presence of an analyte in the exhaled breath of the user 210. The data output by the analyte sensor 174 can be stored in the memory device 114 and used by the control system 110 to determine the identity and concentration of any analytes in the user 210's breath. In some implementations, the analyte sensor 174 is positioned near a mouth of the user 210 to detect analytes in breath exhaled from the user 210's mouth. For example, when the user interface 124 is a facial mask that covers the nose and mouth of the user 210, the analyte sensor 174 can be positioned within the facial mask to monitor the user 210's mouth breathing. In some implementations, the analyte sensor 174 is a volatile organic compound (VOC) sensor that can be used to detect carbon-based chemicals or compounds. In some implementations, the analyte sensor 174 can also be used to detect whether the user 210 is breathing through their nose or mouth. For example, if the data output by an analyte sensor 174 positioned within the facial mask of the user 210 detects the presence of an analyte, the processor 112 can use this data as an indication that the user 210 is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory device 122, etc.). Thus, in some implementations, the moisture sensor 176 can be positioned in the user interface 124 or in the conduit 126 to monitor the humidity of the pressurized air from the respiratory device 122. In other implementations, the moisture sensor 176 is placed near any area where moisture levels need to be monitored. The moisture sensor 176 can also be used to monitor the humidity of the ambient environment surrounding the user 210, for example the air inside the user 210's bedroom.

One or more Light Detection and Ranging (LiDAR) sensors 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor(s) 178 may also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

In some implementations, the one or more sensors 130 also include a galvanic skin response (GSR) sensor, a blood flow sensor, a respiration sensor, a pulse sensor, a sphygmomanometer sensor, an oximetry sensor, a sonar sensor, a RADAR sensor, a blood glucose sensor, a color sensor, a pH sensor, an air quality sensor, a tilt sensor, a rain sensor, a soil moisture sensor, a water flow sensor, an alcohol sensor, or a combination thereof.

While shown separately in FIG. 1, a combination of the one or more sensors 130 can be integrated in and/or coupled to any one or more of the components of the system 100, including the respiratory device 122, the user interface 124, the conduit 126, the humidification tank 129, the control system 110, the user device 170, or a combination thereof. For example, the acoustic sensor 141 and/or the RF sensor 147 can be integrated in and/or coupled to the user device 170. In such implementations, the user device 170 can be considered a secondary device that generates additional or secondary data for use by the system 100 (e.g., the control system 110) according to some aspects of the present disclosure. In some implementations, at least one of the one or more sensors 130 is not coupled to the respiratory device 122, the control system 110, or the user device 170, and is positioned generally adjacent to the user 210 during the sleep session (e.g., positioned on or in contact with a portion of the user 210, worn by the user 210, coupled to or positioned on the nightstand, coupled to the mattress, coupled to the ceiling, etc.).

The data from the one or more sensors 130 can be analyzed to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, a sleep state, an apnea-hypopnea index (AHI), or any combination thereof. The one or more events can include snoring, apneas, central apneas, obstructive apneas, mixed apneas, hypopneas, a mask leak, a cough, a restless leg, a sleeping disorder, choking, an increased heart rate, labored breathing, an asthma attack, an epileptic episode, a seizure, increased blood pressure, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 130, or from other types of data.

The user device 170 (FIG. 1) includes a display device 128. The user device 170 can be, for example, a mobile device such as a smart phone, a tablet, a gaming console, a smart watch, a laptop, or the like. Alternatively, the user device 170 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices can be used by and/or included in the system 100.

While the control system 110 and the memory device 114 are described and shown in FIG. 1 as being a separate and distinct component of the system 100, in some implementations, the control system 110 and/or the memory device 114 are integrated in the user device 170 and/or the respiratory device 122. Alternatively, in some implementations, the control system 110 or a portion thereof (e.g., the processor 112) can be located in a cloud (e.g., integrated in a server, integrated in an Internet of Things (IOT) device, connected to the cloud, be subject to edge cloud processing, etc.), located in one or more servers (e.g., remote servers, local servers, etc., or a combination thereof.

While system 100 is shown as including all of the components described above, more or fewer components can be included in a system for generating physiological data and determining a recommended bedtime for the user according to implementations of the present disclosure. For example, a first alternative system includes the control system 110, the memory device 114, and at least one of the one or more sensors 130. As another example, a second alternative system includes the control system 110, the memory device 114, at least one of the one or more sensors 130, and the user device 170. As yet another example, a third alternative system includes the control system 110, the memory device 114, the respiratory system 120, at least one of the one or more sensors 130, and the user device 170. Thus, various systems for determining a recommended bedtime for the user can be formed using any portion or portions of the components shown and described herein and/or in combination with one or more other components.

Referring generally to FIG. 2, a portion of the system 100 (FIG. 1), according to some implementations, is illustrated. A user 210 of the respiratory system 120 and a bed partner 220 are located in a bed 230 and are laying on a mattress 232. The user interface 124 (e.g., a full facial mask) can be worn by the user 210 during a sleep session. The user interface 124 is fluidly coupled and/or connected to the respiratory device 122 via the conduit 126. In turn, the respiratory device 122 delivers pressurized air to the user 210 via the conduit 126 and the user interface 124 to increase the air pressure in the throat of the user 210 to aid in preventing the airway from closing and/or narrowing during sleep. The respiratory device 122 can be positioned on a nightstand 240 that is directly adjacent to the bed 230 as shown in FIG. 2, or more generally, on any surface or structure that is generally adjacent to the bed 230 and/or the user 210.

In some implementations, the control system 110, the memory 214, any of the one or more sensors 130, or a combination thereof can be located on and/or in any surface and/or structure that is generally adjacent to the bed 230 and/or the user 210. For example, in some implementations, at least one of the one or more sensors 130 can be located at a first position 255A on and/or in one or more components of the respiratory system 120 adjacent to the bed 230 and/or the user 210. The one or more sensors 130 can be coupled to the respiratory system 120, the user interface 124, the conduit 126, the display device 128, the humidification tank 129, or a combination thereof.

Alternatively or additionally, at least one of the one or more sensors 130 can be located at a second position 255B on and/or in the bed 230 (e.g., the one or more sensors 130 are coupled to and/or integrated in the bed 230). Further, alternatively or additionally, at least one of the one or more sensors 130 can be located at a third position 255C on and/or in the mattress 232 that is adjacent to the bed 230 and/or the user 210 (e.g., the one or more sensors 130 are coupled to and/or integrated in the mattress 232). Alternatively or additionally, at least one of the one or more sensors 130 can be located at a fourth position 255D on and/or in a pillow that is generally adjacent to the bed 230 and/or the user 210.

Alternatively or additionally, at least one of the one or more sensors 130 can be located at a fifth position 255E on and/or in the nightstand 240 that is generally adjacent to the bed 230 and/or the user 210. Alternatively or additionally, at least one of the one or more sensors 130 can be located at a sixth position 255F such that the at least one of the one or more sensors 130 are coupled to and/or positioned on the user 215 (e.g., the one or more sensors 130 are embedded in or coupled to fabric, clothing 212, and/or a smart device worn by the user 210). More generally, at least one of the one or more sensors 130 can be positioned at any suitable location relative to the user 210 such that the one or more sensors 130 can generate sensor data associated with the user 210.

Generally, a user who is prescribed usage of the respiratory system 120 will tend to experience higher quality sleep and less fatigue during the day after using the respiratory system 120 during the sleep compared to not using the respiratory system 120 (especially when the user suffers from sleep apnea or other sleep related disorders). For example, the user 210 may suffer from obstructive sleep apnea and rely on the user interface 124 (e.g., a full face mask) to deliver pressurized air from the respiratory device 122 via conduit 126. The respiratory device 122 can be a continuous positive airway pressure (CPAP) machine used to increase air pressure in the throat of the user 210 to prevent the airway from closing and/or narrowing during sleep. For someone with sleep apnea, her airway can narrow or collapse during sleep, reducing oxygen intake, and forcing her to wake up and/or otherwise disrupt her sleep. The CPAP machine prevents the airway from narrowing or collapsing, thus minimizing the occurrences where she wakes up or is otherwise disturbed due to reduction in oxygen intake.

The respiratory device 122 strives to maintain a medically prescribed air pressure or pressures during sleep, but in some cases, the user interface 124 may move or become repositioned while the user 210 is asleep. The movement of the interface 124 can cause and/or allow pressurized air from the respiratory system 120 to leak at an interface between the user interface 124 and face/head of the user 210. For example, the user 210 may sleep on her back while sleeping with the user interface 124 on, but during the course of a night's sleep, the user 210 can unconsciously change position such that her cheek becomes flush against the pillow 260. In such a position, the user interface 124 can move from a relatively snug position with no unintentional air leakage to a new position that allows and/or causes air to unintentionally leak from the respiratory system 120. Unintentional air leaking from the user interface 124 can make audible noise that disturbs the user 210 and/or the bed partner 220, thus interfering with and/or negatively influencing both parties' sleeping session. Further, unintentional air leaking can dry the user's skin, cause dry mouth, cause dry eye(s), etc., or any combination thereof.

Other sources of unintentional air leaks at the interface between the user interface 124 and face/head of the user 210 are possible. For example, over time, the user interface 124 or a portion thereof may become worn such that the seal at the interface is not as complete as when the user interface 124 was new. As another example, straps or strap segments holding a user interface 124 in place can become loosened over time resulting in a poor seal that may cause unintentional leaks.

As used throughout the present disclosure, the term unintentional leak means an unintended flow of air from the respiratory system 120 to ambient. In some implementations, the user interface 124 includes vents designed to allow exhaled gases and air flow from the respiratory system 120, which is referred to as intentional leak or vent flow, as such flow is designed to occur and intended to occur. That is, the gases escaping via the vents are not considered unintentional leaks because the gases comprise an intended flow of air out of the respiratory system 120. In contrast to the intended vent flow out of the respiratory system 120, an unintentional leak may occur, as described above, as the result of an incomplete seal between the user interface 124 (e.g., a mask) and the face/head of the user 210. In some implementations, some flow out of the respiratory system 120 occurs due to an incomplete seal between the user interface 124 and the face/head of user 210, such as where the user interface or a portion thereof (e.g., the cushion) needs to be loose enough for comfort of the user or the user has facial features (e.g., a beard), wherein this is not considered unintentional. In another example, an unintentional leak or air may occur anywhere in the air circuit of the respiratory system 120 to ambient. For example, in some implementations, some flow of air out of the respiratory system 120 can occur anywhere in the circuit of respiratory system 120. For example, a leak at a joint between the conduit 126 and the user interface 124, due to design requirements and/or tolerances, such as ease of movement between the conduit 126 and user interface 124. In some implementations a threshold is set for an unintentional leak where no action is taken until the unintentional leak is greater than the set threshold.

In some implementations, unintentional flow of air out of the respiratory system 120 can be considered acceptable and not deemed to be severe enough to require action (e.g., requiring a new user interface or a new cushion, requiring a change in therapy pressure(s), etc., or any combination thereof). In such implementations, the acceptable amount of unintentional leak or air flow from the respiratory system 120 can be when the volume of the unintentional leak is a certain percentage or less of the total volume of air being flowed by the respiratory system 120. For example, when the unintentional leak is about 20% or less, or about 10% or less, or about 5% or less, or about 3% or less, or about 2% or less, or about 1% or less, etc., the unintentional flow can be deemed acceptable. In terms of air flow, the acceptable unintentional leak can be when the flow of air is less than, for example, about 5 liters per minute, about 4 liters per minute, about 3 liters per minute, about 2 liters per minute, about 1 liter per minute, etc. The amount of time an unintentional lack lasts can also determine if the unintentional leak is acceptable. For example, where the user 210 is transitioning from one sleep position to another causing an unintentional leak, or the user 210 is for a short period of time is in a position that causes an unintentional leak. For example, in some implementations, an unintentional leak can be considered acceptable if it lasts for less than about 1 second, less than about, 5 seconds, less than about 10 seconds, less than about 30 seconds, or less than about one minute. In some implementations, the combination flow rate and time can be considered when determining an acceptable unintentional leak. For example, the unintentional leak can be considered acceptable where during the time of an unintentional leak the total volume of air released due to an unintentional leak is less than about 5 liters, less than about 4 liters, less than about 3 liters, less than about 2 liters, less than about 1 liter.

In some implementations, the unintentional leak is grouped with the intentional leak and referred to as the total leak of the respiratory system 120. In some such implementations, the total leak can be deemed acceptable when below a threshold. For example, when the total leak is below about 30 liters/minute, or below about 29 liters per minute, or below about 28 liters per minute, or below about 27 liters per minute, or below about 26 liters per minute, or below about 25 liters per minute, or below about 24 liters per minute, or below about 23 liters per minute, or below about 22 liters per minute, or below about 21 liters per minute, or below about 20 liters per minute, etc. The acceptableness of the total leak can also be based in part on an amount of time that the total leak is below a threshold. For example, in some implementations, the total leak being below 24 liters per minute for at least 70 percent of a measured amount of time (e.g., a sleep session) can be deemed acceptable.

Figure 3:
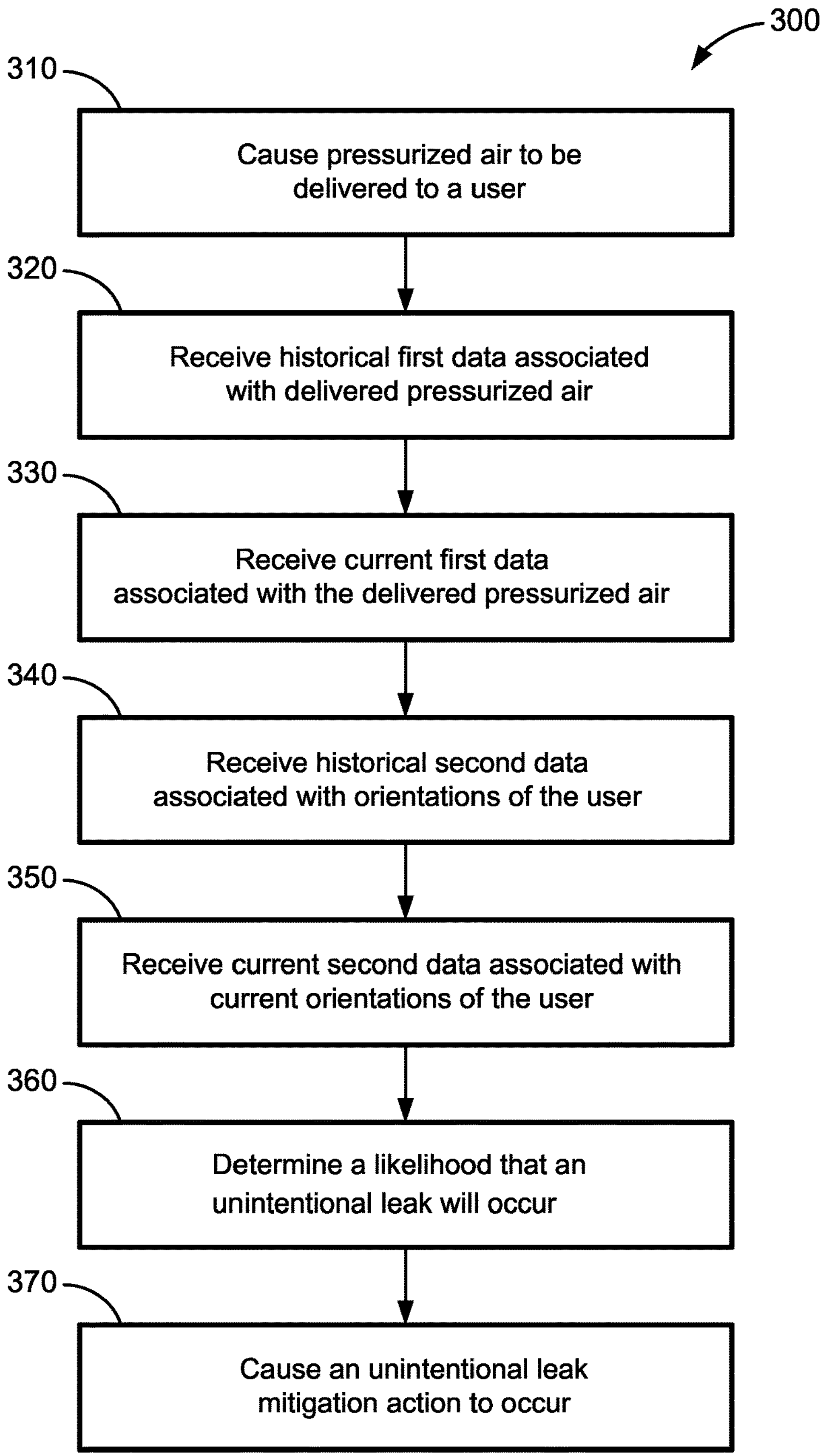
FIG. 3 is a process flow diagram of a method for determining a likelihood that an unintentional leak will occur, according to some implementations of the present disclosure.

Referring to FIG. 3, a flow diagram illustrating a method for predicting an unintentional leak in a respiratory system during a current sleep session is shown according to some implementations of the description.

At step 310, pressurized air is delivered from a respiratory device (e.g., the respiratory device 122) to a user (e.g., the user 210) during the current sleep session. A sleep session is as previously described, and for example, is bounded by the time between when the user 210 has laid or sat down in the bed 230/turned on the respiratory device 122/donned the user interface 124, and when the user 210 removes the user interface 124, turns off the respiratory device 122, and/or gets out of bed 230. The current sleep session refers to the sleep session that is being monitored for prediction of an unintentional leak.

After commencing delivery of pressurized air from the respiratory device in step 310 the method includes four additional steps. At step 320, historical first data associated with the delivered pressurized air is received. At step 330, current first data associated with pressured air delivered is received. At step 340, historical second data associated with orientation of the user is received. At step 350, current second data associated with the orientation of the user is received. The steps 320, 330, 340 and 350 can be made in any order. The steps 320 and 340 can also be implemented before step 310.

Historical first data or historical second data refers to data collected or obtained during a previous sleep session, i.e., not the current sleep session. In some implementation the previous sleep session ends immediately before the beginning of current sleep session, for example during one night or period of time the user 210 intends to sleep. For example, in some implementations the time between the end of previous sleep session and the beginning of the current sleep session is less than about 30 seconds, less than about one minute, less than about 30 minutes, less than about one hour, less than about 4 hours, less than about 12 hours, less than about 18 hours. In some implementation the previous sleep session ends and a longer period of time, such as a period of time spanning the end of a first night and beginning of a second night, occurs before the beginning of current sleep session. For example, in some implementations, the time between the end of the previous sleep session and beginning of the current sleep session is more than about 18 hours, more than about 24 hours, more than about 2 days, more than about 3 days, more than about 4 days, more than 5 days, more than about 6 days, more than about a week, or more than about a month. In some implementations, the previous historical data is an average of one or more sleep sessions that occurred prior to the current sleep session. In some implementations the average is of 1 to 1000 sleep sessions, 1 to 500 sleep sessions, 1 to 100 sleep sessions, 1 to 50 sleep sessions, 1 to 10 sleep sessions, 1 to 3 sleep sessions, or 2 sleep sessions.

Optionally, and according to some implementations, receiving the historical or current first data associated with pressurized air delivered from the respiratory device comprises receiving the first data via one or more first sensors, wherein the one or more first sensors include one or more pressure sensors, one or more flow sensors, one or more humidity sensor, one or more microphones, or any combination thereof. For example, one or more sensors according to system 100 shown in FIGS. 1 and 2. In some implementations the one or more sensors include one or more pressure sensor, one or more flow sensors, or at least one pressure sensor and at least one flow sensor.

In some implementations, receiving the historical or current second data associated with one or more orientations of the user comprises receiving the second data via one or more second sensors including one or more cameras, one or more video cameras, one or more pressure sensors, one or more microphones, one or more speakers, one or more accelerometers, one or more gyroscopes, one or more radio frequency sensors, one or more acoustic sensors, or any combination thereof. Optionally, the radio frequency sensors can be one or more ultra-wideband sensors, one or more impulse radar ultra-wideband sensors or one or more frequency modulated continuous wave radar sensors. For example, one or more sensors according to system 100 shown in FIGS. 1 and 2 can be used.

At step 360, a likelihood that an unintentional leak in the respiratory system will occur is determined. The likelihood that the unintentional leak will occur can be limited to unintentional leaks that will occur within a predetermined amount of time. For example, the likelihood can be associated with an unintentional leak that will occur within ten seconds, within thirty second, within one minute, within five minutes, within ten minutes, etc., or any other amount(s) of time. In some implementations, the likelihood is determined using the historical first pressure data (step 320), the historical second data associated with the orientation of the user (step 340), the current first pressure data associated with pressurized air delivered (step 330), the current second data associated with the orientation of the user, or any combination thereof.

At step 370, an unintentional leak mitigation action is caused to occur, where the mitigation action is responsive to the likelihood satisfying a threshold that an unintentional leak occurs. The likelihood can be expressed, for example, as a probability e.g., as express with integers selected from 1 and 10 (e.g., 1 to 5, 1 to 3, or any range), such as where 1 is least likely and 10 is most likely. In some other implementations, the likelihood is expressed as a rating such as, very unlikely, unlikely, medium likely, likely, and very likely. Other implementations may express the likelihood as a percentage likelihood. According to some implementations, the likelihood is percentage likelihood that an unintentional leak occurs with a threshold is at least about 50%, at least about 60%, at least about 70%, at least about 80%, at least about 90% or at least about 99%.

In some implementations the mitigation action includes causing a sound to be emitted, causing a therapy pressure to change, cause an Expiratory Pressure Relief (EPR) setting to change, causing a humidification level to change, causing a device to be modified or move, causing a light to turn on or increase in brightness, causing a fan to turn on or increase in output, or any combination thereof. In some implementations the kind of mitigation action that occurs depends on the percent likelihood that an unintentional leak will occur. For example, if a threshold of 60% causes a first mitigation action to occur, and the likelihood increases to 90% because the first mitigation action is not effective or even causes an increase in the likelihood, a second mitigation action can occur. If the likelihood of an unintentional leak still increases escalation by a third or more mitigation actions can occur. In some implementations a mitigation action can be implemented even after an unintentional leak has occurred. In some implementations a second mitigation might occur even if the likelihood stays the same or even decreases after a first mitigation action, for example where a likelihood remains above a threshold.

Sounds that can be used as mitigation action can include, without limitation, white noise, pink noise, brown noise, violet noise a soothing sound, music, an alarm, an alert, beeping, or a combination thereof. As used herein, some variants of the flat shaped white noise sound are referred to as pink noise, brown noise, violet noise, etc. In some implementations the sounds (e.g., white noise, pink noise, brown noise, violet, etc.) aid in masking noises from an unintentional leak that is predicted to occur. In some implementations, the sounds (e.g., soothing sounds and music) aid the user or bed partner to remain in a sleep state or can gently awaken or cause the user to change sleeping position, e.g., to a position where an unintentional leak will not or is less likely to occur.

In some implementations the sound can be provide by the one or more speakers 142 of system 100. Optionally, the system 100 includes multiple speakers 142 to provide localized sound emission. The speakers 142 can include in the ear speakers, over the ear speakers, adjacent to the ear speakers, ear buds, ear pods, or any combination thereof. The speakers 142 can be wired or wireless speakers (e.g., headphones, bookshelf speakers, floor standing speakers, television speakers, in-wall speakers, in-ceiling speakers, etc.). In some implementations, the speakers 142 are worn by the user 210 and/or the bed partner 220. In some such implementations, the provided speakers 142 can supply the masking noise without impacting the bed partner as the sound would be localized via the type of the speakers 142. In such implementations, respective localized speakers 142 could be provided for the respiration user and/or the bed partner.

Optionally, the speaker 142 is attached to one or more of a strap or strap segments of the user interface 124. Thus, the user 210 and/or the bed partner 220 has the choice to perceive a relatively flat shaped white noise sound, or for a quieter (lower level and/or low pass filtered) shaped noise signal. In some such implementations, the higher frequency sounds/noises (e.g., "harsher" sounds) are reduced, while still providing masking sounds to the environmental noise. The system 100 can select an optimized set of fill-in sound frequencies to achieve a target noise profile. For example, if certain components of sound already exist in the frequency spectrum (e.g., related to a box fan in the room, a CPAP blower motor, etc.), then the system 100 can select fill-in sounds with sound parameters/characteristics that fill in the quieter frequency bands, for example, up to a target amplitude level. Thus, the system 100 is able to adaptively attenuate the higher and/or lower frequency components using active adaptive masking and/or as adaptive noise canceling such that the perceived sound is more pleasant and relaxing to the ear (the latter being more suited to more slowly varying and predictable sounds).

In some implementations, the sound is caused to be emitted in a gradual fashion. For example, the control system 100 can cause the speaker 142 to emit the sound at a first volume and then incrementally increase the volume from the first volume to a second louder volume over a period of time. For example, the speaker 142 can emit sound at a relatively low volume initially then gradually increase the volume so as to not wake and/or disturb the user 210 and/or the bed partner 220 with a sudden introduction of a new sound. The time period for the ramping up the volume can be 1 second, 5 seconds, 10 seconds, 20 seconds, 30 seconds, etc. or any other amount of time. In some implementations, the sound can start at a low volume responsive to the likelihood satisfying a threshold, and, if the likelihood does not decrease, for example due to the user 210 changing orientation, then the sound can gradually increase until the likelihood decreases. In some implementations, once the likelihood no longer satisfied the threshold (e.g., it is below a threshold) the sound can stop instantaneously or the sound can gradually decrease, e.g., until no sound is emitted. The time period for the ramping down the volume can be about one second, about five seconds, about ten seconds, about twenty seconds, about thirty seconds, etc., or any other amount of time.

Pressure therapy changes that can be used as a mitigation action can include, without limitation, increasing the pressure of air delivered to the user 210 or decreasing the pressure delivered to the user 210. The increase and decrease in pressure can be related to the orientation of the user 210. For example, where a user 210 shifts to an orientation where the user interface 124 is moved so that the likelihood of an unintended leak increases (e.g., against a mattress 232 or pillow 260), the pressure can be decreased to reduce the likelihood of an unintended leak occurs. In some implementations the pressure can be increased to arouse the user 210 or cause a slight discomfort causing the user 210 to change orientation, without necessarily waking the user up.

Expiratory Pressure Relief (EPR) settings can be changed in response to an unintentional leak prediction. In general, EPR is a feature on some respiratory devices (e.g., CPAP machines) that allows users to adjust between different comfort settings to alleviate feelings of breathlessness some users experience. For example, a drop of 2 cm $H_2O$ between inspiration and expiration. Where this feature can be manual, the EPR setting can be changed by the system 100 without manual user input according to implementations of this description to mitigate against an unintentional leak occurring.

In some implementations the change in humidification level used as a mitigation action is an increase in the humidity of the air delivered to the user 210. For example, where the percent likelihood of an unintentional leak increases due to a drying out of the skin of user 210 causing a seal between the interface 123 and user 210 to be less efficient. The user 210 might also experience discomfort due to dryness of the nose or mouth at a lower humidification level, the discomfort leading to orientation changes that are predicted to increase the likelihood of an unintentional leak. In some implementations the change in humidification level is a reduction in humidification. For example, where the user 210 experiences discomfort due to moistness or water accumulation (e.g., at the seal of the user interface 124) leading to orientation changes that are predicted to increase the likelihood of an unintentional leak.

A device that is actuated or moved as a mitigation action can include, without limitation, a smart pillow, an adjustable bed frame, an adjustable mattress, a fan, an adjustable blanket, or any combination thereof. For example, the device is under control of controller 110. In some implementations the smart pillow, smart mattress, or adjustable blanket can include one or more inflatable compartments or bladders that can inflate or deflate. The actuated device can thereby change the orientation of user. For example, a pillow 260 can be a smart pillow including one or more inflatable bladders that change the orientation of user 210 if the user's head is in an orientation that increases the likelihood of an unintentional leak above a threshold. In another or additional implementation, an adjustable bed frame can include sections that can rise or lower as driven by a motor and cause the user 210 to change orientation, e.g., forcing user 210 to roll from their side to their back. In some implementations, the fan, for example a fan placed on nightstand 240, a fan in a window or a ceiling fan, turns on responsive to the likelihood of an unintentional leak and blows air towards user 210 to induce or cause them to change orientation. As another option, the fan turns off responsive to the likelihood of an unintentional leak satisfies a threshold. In some implementations, the fan turns on or off to provide a more soothing environment to the user 210 who is predicted to change orientations to a position where an unintentional leak occurs due to discomfort associated with an air current or lack thereof. In some implementations, the fan generates white noise. The fan can increase in speed and movement of air gradually, so as to not wake and/or disturb the user 210 and/or the bed partner 220 with a sudden change of air movement or sound from the fan.

In some implementations the leak mitigation action caused to occur is injection of a substance into the pressurized air to be being delivered to the user interface 124. For example, receptacle 180 can be charged with a substance, the receptacle having an outlet that is in direct or indirect fluid communication with the conduit 126. The substance can be configured or selected to invoke a physical reaction by the user 210. For example, the user 210 may change orientation.

Optionally, the substance can include a medicament, such as anti-inflammatory medicine, medicine to treat an asthma attack, medicine to treat a heart attack, etc. Generally, any type of medicament that is used to treat any ailment, symptom, disease, etc. can be delivered to the airway of the user 210. For example, where symptoms cause agitation or orientation changes and movement of the user 210 that increase the likelihood of an unintentional leak, injecting the medicament can reduce the likelihood of an unintentional leak. When the substance is a medicament, the substance generally includes one or more active ingredients, and one or more excipients. The excipients serve as the medium for conveying the active ingredient, and can include substances such as bulking agents, fillers, diluents, antiadherents, binders, coatings, colors, disintegrants, flavors, glidants, lubricants, preservatives, sorbents, sweeteners, vehicles, or any combinations thereof. The active ingredient is generally the portion of the medicament that actually causes the effect brought on by the medicament.

The substance can also optionally be an aroma compound (e.g., a substance that delivers scents and/or aromas to the airway of the user 210), a sleep-aid (e.g., a substance that aids the user 210 in falling asleep), a consciousness-arousing compound (e.g., a substance that aids the user 210 in waking up, also referred to as a sleep inhibitor), a cannabidiol oil, an essential oil (such as lavender, valerian, clary sage, sweet marjoram, roman chamomile, bergamot, etc.). The substance can generally be a solid, a liquid, a gas, or any combination thereof. The substance can alternatively or additionally include one or more nanoparticles.

In some implementations, the current second data is indicative that the user moved from a first position to a second position. For example, wherein the first position is any of resting on its back, resting on its side, resting on its stomach and resting in a fetal position. The second position is one of resting on its back, resting on its side, resting on its stomach and resting in a fetal position different from the first position. Optional the first position involves the user resting on its back and the second position involves the user resting on its side. Optionally, the first position the user resting on its back and the second position involves the user resting on its stomach. Optionally, the first position involves the user resting on its side and the second position involves the user resting in a fetal position.

Alternatively or optionally, after an unintentional leak mitigation action occurs at step 370, the likelihood that an unintentional leak occurs is re-evaluated. For example, by repeating one or more of the steps 330, 340, 350, 360 and 360 outlined in FIG. 3. Where, upon repetition, the likelihood of an unintentional leak does not satisfy a threshold after the re-evaluation at step 360, additional mitigation actions can occur e.g., step 370. These steps can be implemented repeatedly for predicting and mitigating an unintentional leak through the sleep session, such as more than 3 times, more than 10 time, more than 20 times, more than 30 times. In some implementations, the number of times a mitigation action is used is tracked and stored, e.g., in memory device 114. In some implementations, this information can be displayed, for example, to the use 210 or a caregiver. This can be displayed, for example, after one or more sleep sessions using an external device 170 such as a smart phone.

The data received in any one of the steps 320, 330, 334, 335 can be processed by a respiratory system 100. For example, the control system can include an unintentional leak prediction algorithm stored in a memory such as memory device 114 as machine-readable instructions. The unintentional leak prediction algorithm can be initiated, for example, when a sleep session is started. For example, a start of a sleep session is detected by one or more sensors 130. In some implementations, the sleep session starts, and the algorithm initiates, when pressurized air is delivered to the user (step 310). In some implementations, the algorithm can be started but in a sleep or monitoring mode until a sleep session starts, after which it is considered initiated. In some implementations, the sleep session is started manually by the user 210, and the algorithm is initiated, such as by turning on the respiratory device 122, donning user interface 124 or reclining in bed. Once pressurized air is delivered to the user, data from one or more of steps 320, 330, 340, and 350, can be received by the algorithm as input. The algorithm can output an unintentional leak prediction value, for example based on the likelihood calculated, by the algorithm, at step 360 for the individual. The determined unintentional leak prediction value is indicative of a likelihood that the user will experience an unintentional leak within a predetermined amount of time in the current sleep session. In some implementations, the pre-determined amount of time is less than about 5 seconds, less than about 10 seconds, less than about 20 seconds, less than about 30 seconds, less than about 40 seconds, less than about 50 seconds, less than about 60 seconds, less than about 2 minutes, less than about 5 minutes, less than about 10 minutes, or less than about one hour. Steps prior to processing using the unintentional leak prediction algorithm can include receiving data via one or more sensors 130 as previously described, and transferring or sending the data to the control system, including storing the data in memory device 114. In some implementations, the system 100 can active or actuate a device to mitigate an unintentional leak from occurring.

In some implementations the method for predicting an unintentional leak further includes identifying a type of the user interface. For example, in some implementations, the method includes identifying the user interface such as a full face mask, a nasal face mask or nasal pillow. In some implementations determining the likelihood of an unintentional leak is further based at least in part on the identified type of the user interface. In some other implementations the user interface is identified from a chart such as a model and make that is referred to.

Figure 4:
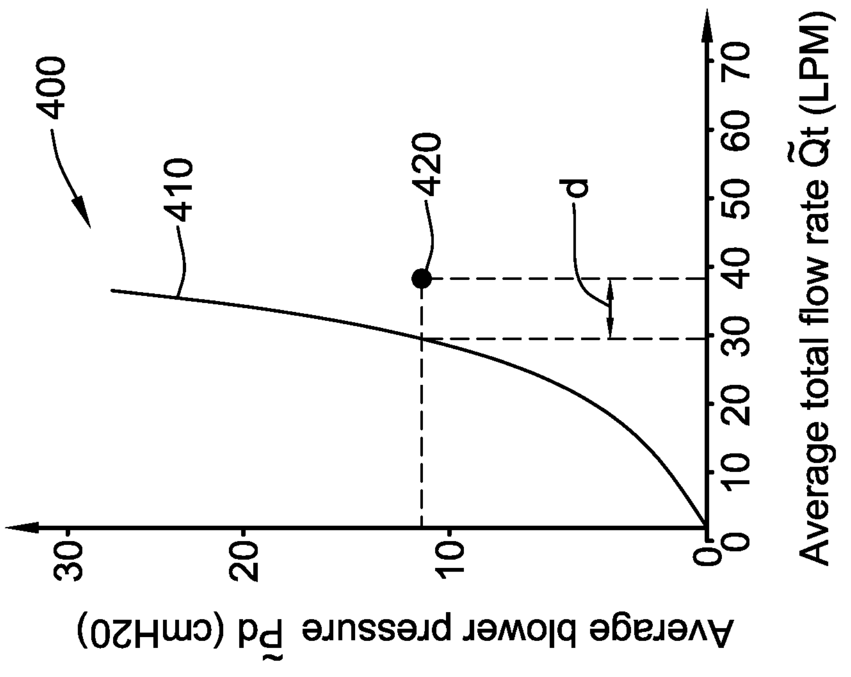
FIG. 4 is a plot of pressure and flow data, according to some implementations of the present disclosure.

Predicting an unintentional leak and identifying a user interface and can optionally be based on measuring pressure and flow in respiratory system 120. The pressure and flow data are used for generating a plot 400 having an intentional leak characteristic curve 410 as shown by FIG. 4. Generally, an unintentionally leak can be predicted by an excursion in pressure and flow from characteristic curve 410. Also, in general, the shape of the characteristic curve 410 can identify the user interface.

In FIG. 4 the average total flow rate Qt (in liters per minute) versus average device pressure Pd (in $cmH_2O$) is depicted, where the average values are averages over a plurality of respiratory cycles. The shape of curve 410 depends on the mask such as the shape and volume (e.g., enclosed by the users face and the mask) and the mask vent size and configuration. Accordingly, the type of mask can be determined by the shape of curve 410. The average flow Qt as described by curve 410 corresponds to the flow out of the device system, such as respiratory system 120, where the flow is the intentional flow, such as flows out of vents in a mask (e.g., user interface 124). Accordingly, excursions away from curve 410 relate to unintended flow.

As a user 210, breaths in an out wearing an interface, such as user interface 124, the device 122, such as a CPAP, tries to maintain a constant pressure. However, some small fluctuations occur around the targeted or set pressure, which correspond to the average pressure Pd increasing and decreasing slightly. With intended flow (i.e., no unintended flow), as Pd oscillates up and down, the average flow value Qt follows curve 410 exactly. Unintentional leaks correspond to excursions off of and to the right of the curve 410, such as average pressure and flow (Pd, Qt) point 420. At point 420, with an average pressure Pd of about 11 ($cmH_2O$), if an expected leak occurred the average flow Qt would be about 30 LPM. However, since the average flow Qt is actually measured at almost 40 LPM an unintentional leak is indicated, with a delta d of about 40 LMP from the characteristic curve.

Another unintended flow, herein referred to an unintentional block, can also occur if there is a blockage in the system, such as where a user's position blocks a mask vent or conduit 126 becomes blocked (e.g., bent, or kinked). In these instances, the flow will be lower than predicted by the intentional leak plot 410. An unintentional block would appear as a point or excursion to the left of curve 410. In some implementations, unintentional block data can be used to receive the historical second data associated with one or more orientations of the user during one or more prior sleep sessions. In some implementations the unintentional block data can be used to receive current data associated with one or more orientations of the user during the current sleep session.

Increasing the pressure applied to a user interface can increase the incidences of unintentional leaks. For example, the increase in pressure can cause the seal between a mask (e.g., user interface 124) and the user's face to be degraded and allow air to escape. Although a user might increase and improve a seal between user and mask by tightening straps of a user interface, at some high enough pressure, some amount of unintentional leak will occur.

In some implementations the intentional flow curve 410 as depicted in FIG. 4 is derived as follows. A flow pathway is formed by a respiratory device (e.g., the respiratory device 122), a mask (e.g., the user interface 124) having one or more vents, and a conduit (e.g., the conduit 126). The conduit creates a first impedance Z1, which in turn causes a pressure drop ΔP that is a function of the total flow rate Qt. The interface pressure Pm is the device pressure Pd less the pressure drop ΔP through the conduit, where ΔP(Q) is the pressure drop characteristic of the conduit:

$$Pm=Pd-\Delta P(Qt). \tag{1}$$

The vent of the mask creates a second impedance Z2. The vent flow Qv is related to the interface pressure Pm via the vent characteristic f:

$$Pm=f(Qv). \tag{2}$$

Combining equation (1) with equation (2), the device pressure Pd may be written as $$Pd=f(Qv)+\Delta P(Qt). \tag{3}$$

The unintentional leak, which is unknown and unpredictably variable, creates a third impedance Z3. The fourth impedance Z4, the capacitance Clung, and the variable pressure source Plung represent characteristics of the user. Thus, the total flow rate Qt is equal to the sum of the vent flow rate Qv, the leak flow rate Qleak, and the respiratory flow rate Qr:

$$Qt=Qv+Qleak+Qr. \tag{4}$$

In some implementations, the respiratory flow rate Qr averages to zero over a plurality of respiratory cycles (e.g., breathing cycles), because the average flow into or out of the lungs must be zero. As such, taking an average of each flow rate over the plurality of respiratory cycles, the vent flow rate may be approximated as:

$$\tilde{Q}v=\tilde{Q}t-\tilde{Q}leak. \tag{5}$$

The tilde (~) indicates the average value over the plurality of respiratory cycles. The process of averaging may be implemented by low-pass filtering with a time constant long enough to contain the plurality of respiratory cycles. The time constant can be of any suitable duration, such as five seconds, ten seconds, thirty seconds, one minute, etc. However, other time intervals are also contemplated.

Combining equations (3) and (5), the average device pressure Pd may be written as $$\tilde{P}d=f(\tilde{Q}t-\tilde{Q}leak)+\Delta P(\tilde{Q}t). \tag{6}$$

Absent any leak flow (e.g., Qleak=0), the average total flow rate $\tilde{Q}t$ may be referred to as the bias flow rate Qb. Equation (6) can then be written to reflect the relationship between bias flow rate Qb and average device pressure Pd that characterizes the respiratory therapy system:

$$\tilde{P}d=f(Qb)+\Delta P(Qb). \tag{7}$$

The relationship, which is the intentional leak characteristic curve for the system, is determined by the vent characteristic f(Q) and the conduit pressure drop characteristic ΔP(Q).

The characteristic intentional flow plot as shown in FIG. 4 can be made by measuring average total flow rate $\tilde{Q}t$ (in liters per minute) versus average device pressure $\tilde{P}d$ (in $cmH_2O$) for at least two pressures, or two average flows. The plotted $\tilde{P}d$ and $\tilde{Q}t$ data points can be fitted and described by an equation. For example, in some implementations, the intentional leak characteristic curve 410 may be approximated using a polynomial equation, such as a quadratic equation:

$$\tilde{P}_d=k_1Q_b^2+k_2Q_b. \tag{8}$$

The parameters of the intentional leak characteristic curve, in this quadratic equation, two non-zero constants (or coefficients), $k_1$ and $k_2$, characterize the series concatenation of the vent characteristic f and the air circuit pressure drop characteristic ΔP. In some implementations, the polynomial equation defines an intentional leak of the system (e.g., vent flow of the system) by providing a corresponding flow rate of intentional leak for a given pressure.

In some implementations, the polynomial equation may have more than two non-zero constants, such as three non-zero constants, four non-zero constants, five non-zero constants, etc. For example, the polynomial equation may be expressed as:

$$\tilde{P}_d = k_1 Q_b^2 + k_2 Q_b + k_3. \tag{9}$$

In some implementations, the polynomial equation may involve a power of three, four, five, etc. For example, the polynomial equation may be expressed as:

$$\tilde{P}_d = k_1 Q_b^3 + k_2 Q_b^2 + k_3 Q_b. \tag{10}$$

In some implementations, the polynomial equation may involve a power of three, four, five, etc. For example, the polynomial equation may be expressed as:

$$\tilde{P}_d = k_1 Q_b^3 + k_2 Q_b^2 + k_3 Q_b. \tag{11}$$

As discussed herein, a respiratory therapy system typically includes components such as a respiratory device 122, a conduit 126, and a user interface 124. A variety of different models may be used which can impact the pressure and flow characteristics. For example, models can include different vents in a face mask and different lengths and diameters of conduits. In order to provide improved control of therapy delivered to the user interface, it may be advantageous to estimate treatment parameters such as the pressure in the user interface, the vent flow rate, and the unintentional flow rate. In systems using estimation of treatment parameters, knowledge of the type of component being used by a user can enhance the accuracy of treatment parameter estimation, and therefore the efficacy of therapy.

To obtain knowledge of component type, some respiratory devices include a menu system that allows the user to enter and/or select the type of system components, including the user interface being used (e.g., brand, manufacturer, form, model, serial number, mask family, size etc.). Once the types of the components are entered and/or selected by the user, the respiratory device can select appropriate operating parameters of the flow generator that best coordinate with the selected components, and can more accurately monitor treatment parameters during therapy. However, in some instances, the user may not select the type of component correctly, or at all, leaving the respiratory device in error or ignorant about the type of component in use.

As such, in some implementations, an unintentional leak prediction algorithm can include code or sub routine used to identify the user interface. For example, if the conduit pressure drop characteristic ΔP is known, (e.g., because the type of conduit making up the conduit is known, or through a prior calibration operation), then the parameters of the intentional leak characteristic curve effectively characterize the vent, which in turn is indicative of the type of user interface.

In some implementations, the historical first data and historical second data are received with a user 210 using the same user interface 124. In some implementations, the historical first data, historical second data, current first data, and current second data are received with a user 210 using a first user interface 124, and the current first data, and current second data are received with a user 210 using a second user interface 124. In some such implementations, the unintentional leak prediction algorithm can adjust or compensate to changes due to the user interface change.

In some implementations, the identification of user interface may be done by comparing the computed parameters $k_1$ and $k_2$ to a data structure such as an array or database having pairs ($k_1$, $k_2$) associated with known user interface types, when used with the known conduit. The type of user interface associated with the stored pair ($k_1$, $k_2$) that most closely matches the computed parameters $k_1$ and $k_2$ may be taken as the type of the user interface.

Alternatively, the pressure drop $\Delta P(\tilde{Q}t)$ may be subtracted from each value of the average device pressure $\tilde{P}d$ before fitting the quadratic equation to the resulting mask intentional leak characteristic curve. The resulting parameters $k_1$ and $k_2$ may then be compared to a data structure of pairs ($k_1$, $k_2$) associated with known user interface types to identify the user interface or access data for operations of the respiratory device that is associated with use of particular user interfaces.

Thus, the detected parameters can be compared to the expected parameters over a period of time, collecting longitudinal data and cross-sectional data. In some implementations, the system may be able to determine production variation by understanding a batch of masks, and use this for production quality improvement.

In some implementations, the system can check for variation over time, and understand if the mask seal itself is degrading over time (as the system can determine how long a specific mask has been in use based on a signature such as an acoustic signature), and what are the conditions that are giving rise to unintentional leak (e.g., is it position dependent, has it changed based on recommendation to tighten or loosen headgear, has the seal followed an expected degradation cycle (assuming regular washing), is it showing accelerated wear, etc.).

In some implementations, the user interface being used can be determined by: user input, detecting the user interface optically, detecting the user interface via RFID, detecting the user interface via echo signature, detecting the conduit via connector of heated tube that has electronics, or any combination thereof. Thus an initial curve can be selected that describes a correctly functioning new mask of this type. The initial curve may be specific to the respiratory device, the operating mode, the operating parameters, other settings such as Expiratory Pressure Relief (EPR) or bi-level, the user interface (e.g., brand, manufacturer, form, model, serial number, mask family, size etc.), or any combination thereof.

In some implementations, overtime, the system may also be able to select models of expected behavior of partially worn or fully worn out masks of this type as the initial curve, such as from a look up table, or from a cloud system. These expected models may describe different levels of vent occlusion, conduit occlusion (such as for masks that have airflow through soft tubing around the head) and different levels of seal wear, headgear stretching and so forth. Thus, by selecting an appropriate initial model, the system can detect intentional leak and unintentional leak through a sleep session, and/or across multiple sleep sessions.

In some implementation the system provides an output to an external device 170 such as a smart phone that provides the user data related to the amount of predicted unintentional leaks detected or the % likelihood of unintentional leaks detected. For example, during a sleep session or over several sleep sessions.

One or more elements or aspects or steps, or any portion(s) thereof, from one or more of any of claims below can be combined with one or more elements or aspects or steps, or any portion(s) thereof, from one or more of any of the other claims or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method of predicting an unintentional leak in a respiratory system during a current sleep session, the method comprising:

causing, during the current sleep session, pressurized air to be delivered from a respiratory device to a user via a conduit coupled to a user interface, the user interface being worn about a portion of a face of the user to aid in the user receiving at least a portion of the pressurized air;

receiving historical first data associated with pressurized air delivered from the respiratory device during one or more prior sleep sessions;

receiving, via one or more first sensors, current first data associated with the pressurized air being delivered from the respiratory device during the current sleep session;

receiving historical second data associated with one or more orientations of the user during one or more prior sleep sessions;

receiving, via one or more second sensors, current second data associated with one or more orientations of the user during the current sleep session, wherein the one or more second sensors include a speaker generating a sound wave at a predetermined interval and a microphone detecting reflections of the emitted sound wave, wherein the current second data includes the reflections of the emitted sound wave;

determining, based at least in part on the (i) historical first data, (ii) the current first data, (iii) the historical second data, and (iv) the current second data, a likelihood that an unintentional leak in the respiratory system will occur within a predetermined amount of time; and responsive to the likelihood satisfying a threshold, cause one of a sound to be emitted, one or more pressure settings of the therapy to change, a humidification level to change, a device to move, or cause a substance to be injected into pressurized air delivered to a user interface.

2. The method of claim 1, wherein the sound includes white noise, pink noise, brown noise, violet noise, a soothing sound, music, an alarm, an alert, beeping, or any combination thereof.

3. The method of claim 1, further comprising, responsive to the likelihood satisfying the threshold, cause an Expiratory Pressure Relief (EPR) setting to change.

4. The method of claim 1, wherein the substance is configured to invoke a physical reaction by the user.

5. The method of claim 1, wherein the one or more first sensors include one or more pressure sensors, one or more flow sensors, one or more humidity sensors, one or more microphones, or any combination thereof.

6. The method of claim 1, wherein the one or more second sensors include one or more cameras, one or more video cameras, one or more pressure sensors, one or more accelerometers, one or more gyroscopes, one or more radio frequency sensors, one or more acoustic sensors, or any combination thereof.

7. The method of claim 1, further comprising identifying a type of a user interface.

8. The method of claim 7, wherein the identified type of user interface is a full face interface, a nasal interface, or a nasal pillow interface.

9. The method of claim 1, wherein the current second data is indicative that the user moved from a first position to a second position.

10. The method of claim 9, wherein the first position involves the user resting on their back and the second position involves the user resting on their side or on their stomach.

11. A method of predicting an unintentional leak in a respiratory system during a current sleep session, the method comprising:

determining, for a user of the respiratory system, an unintentional leak prediction value, the determined unintentional leak prediction value being indicative of a likelihood that the user will experience an unintentional leak within a pre-determined amount of time in the current sleep session, the unintentional leak prediction value being determined using a unintentional leak prediction algorithm that is configured to receive, as an input, positional data, and output the unintentional leak prediction value for the individual, wherein the positional data is determined by a speaker generating a sound wave at a predetermined interval and a microphone detecting reflections of the emitted sound wave; and responsive to the unintentional leak prediction value satisfying a threshold, causing at least one oof a sound to be emitted, a therapy pressure to change, a humidification level to change, a device to be modified, a light to turn on, a fan to turn on, or any combination thereof to occur.

12. The method according to claim 11, wherein the algorithm is further configured to receive, as an input, physiological data associated with the user of the respiratory system.

13. A respiratory system comprising:

a respiratory device delivering pressurized air to a user interface configurable to be worn by a user;

a first sensor receiving current first data associated with the pressurized air being delivered from the respiratory device during a current sleep session;

a second sensor receiving current second data associated with one or more orientations of the user during the current sleep session, wherein the second sensor include a speaker generating a sound wave at a predetermined interval and a microphone detecting reflections of the emitted sound wave, wherein the current second data includes the reflections of the emitted sound wave;

a storage device storing historical first data associated with pressurized air delivered from the respiratory device during one or more prior sleep sessions and historical second data associated with one or more orientations of the user during one or more prior sleep sessions; and a processor coupled to the storage device and first and second sensors, the processor operable to:

determine, based at least in part on the (i) historical first data, (ii) the current first data, (iii) the historical second data, and (iv) the current second data, a likelihood that an unintentional leak in the respiratory system will occur within a predetermined amount of time;

determine whether the likelihood satisfies a threshold; and in response to the likelihood satisfying the threshold cause one of a sound to be emitted, one or more pressure settings of the therapy to change, a humidification level to change, a device to move, or a substance to be injected into pressurized air delivered to a user interface.

14. The system of claim 13, wherein the first sensor is one of a group consisting of one or more pressure sensors, one or more flow sensors, one or more humidity sensors, one or more microphones, or any combination thereof.

15. The system of claim 13, wherein the second sensor is one of a group consisting of one or more cameras, one or more video cameras, one or more pressure sensors, one or more accelerometers, one or more gyroscopes, one or more radio frequency sensors, one or more acoustic sensors, or any combination thereof.

16. The system of claim 13, wherein a first position involves the user resting on their back and a second position involves the user resting on their side or on their stomach.

* * * * *